United States Patent [19]

Willis

[11] Patent Number: 4,582,050

[45] Date of Patent: Apr. 15, 1986

[54] THERAPEUTIC BED WITH TRACTION ASSEMBLY

[76] Inventor: William J. Willis, 108 Adirondack Dr., Selden, N.Y. 11784

[21] Appl. No.: 678,107

[22] Filed: Dec. 4, 1984

[51] Int. Cl.[4] .................... A61F 5/00

[52] U.S. Cl. .................... 128/73; 128/33; 128/70; 269/323; 5/62; 5/433

[58] Field of Search .................... 128/33, 69, 70, 71, 128/72, 73, 74, 75; 269/322, 323, 324, 325, 326; 5/60, 61, 62, 63, 64, 65, 433, 509, 66, 67, 68, 69

[56] References Cited

U.S. PATENT DOCUMENTS

| | | | |
|---|---|---|---|
| 997,284 | 7/1911 | Fuller | 5/62 |
| 1,170,119 | 2/1916 | Sefton | 128/72 |
| 1,276,655 | 8/1918 | Housholder | 128/72 |
| 1,936,363 | 11/1933 | Murray | 128/74 |
| 2,186,660 | 1/1940 | Alopaeus | 269/325 |
| 2,756,743 | 7/1956 | Clark | 128/33 |
| 2,856,916 | 10/1958 | Gilbert | 128/33 |
| 2,949,911 | 8/1960 | Kennard | 128/33 |
| 3,081,085 | 3/1963 | De Girolamo | 128/70 |
| 3,238,936 | 3/1966 | Siedentop | 128/71 |
| 3,306,284 | 2/1967 | McKinley | 128/75 |
| 3,568,669 | 3/1971 | Stites | 128/71 |
| 3,676,881 | 7/1972 | Duprey | 5/510 |
| 3,766,912 | 10/1973 | Daniels | 128/71 |
| 4,166,459 | 9/1979 | Nightingale | 128/75 |

FOREIGN PATENT DOCUMENTS

| | | | |
|---|---|---|---|
| 1256353 | 9/1965 | Fed. Rep. of Germany | 5/82 |
| 1123 | of 1897 | United Kingdom | 269/325 |
| 1319593 | 6/1973 | United Kingdom | 5/63 |

*Primary Examiner*—Edgar S. Burr

*Assistant Examiner*—William L. Klima

*Attorney, Agent, or Firm*—Leonard Belkin

[57] ABSTRACT

A therapeutic bed useful in the home and institutions for the application of traction to a patient having a stationary frame and a moveable frame. Traction is applied by supporting the patient either at a point below the chin or at the feet and tilting the moveable frame so that the weight of the patient produces the traction.

8 Claims, 17 Drawing Figures

FIG. 5
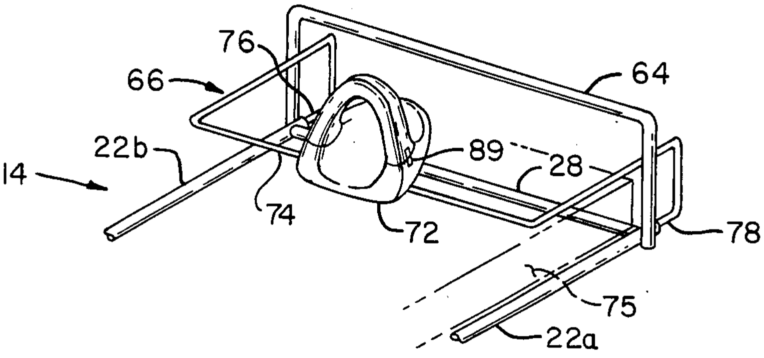
FIG. 6
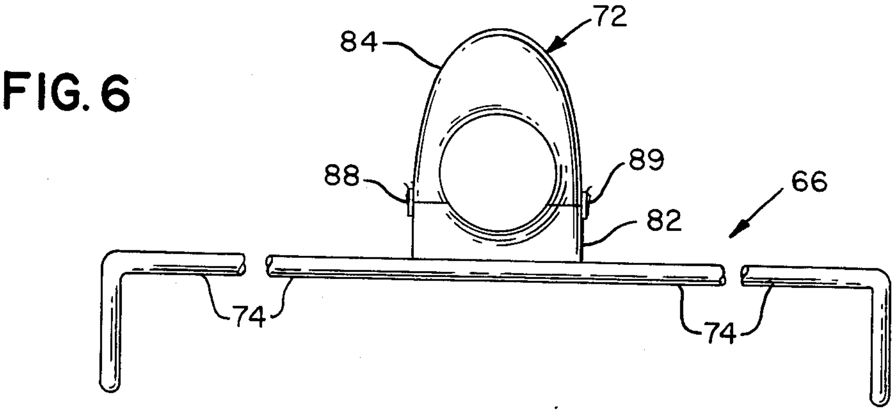
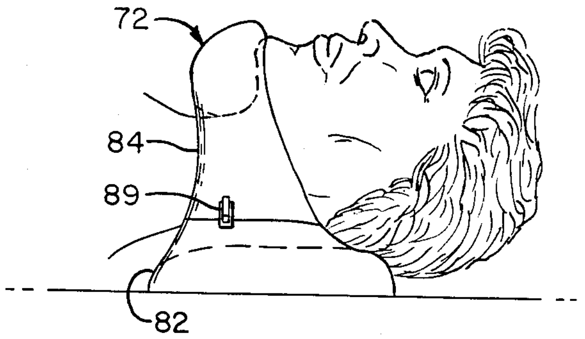
FIG. 6a
FIG. 9
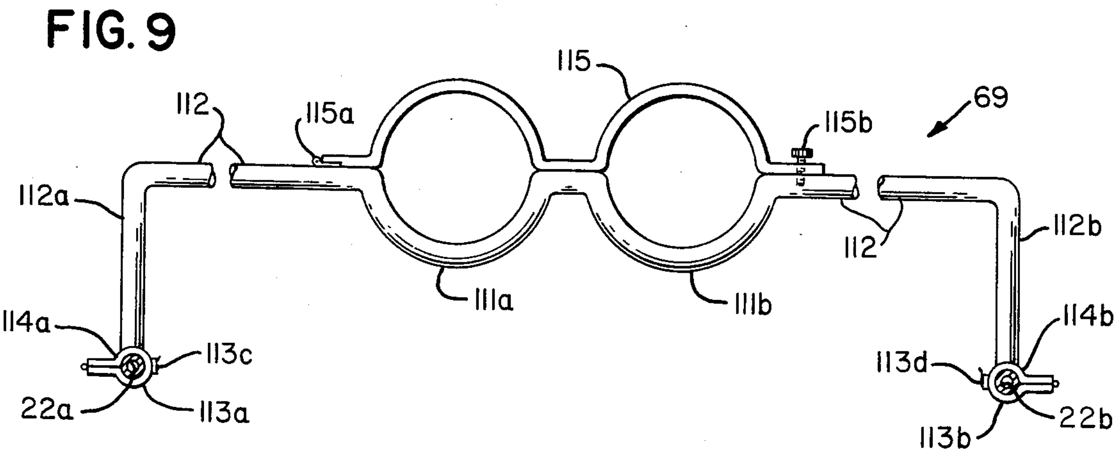

FIG. 11
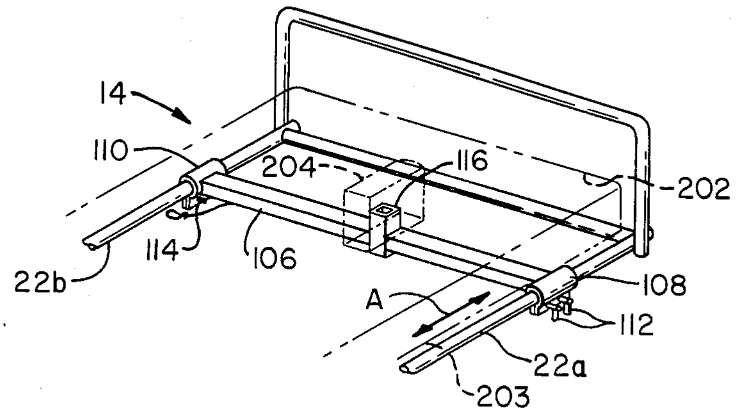
FIG. 13
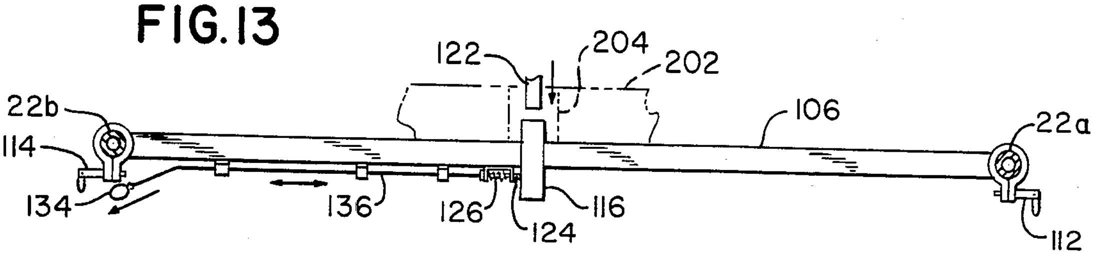
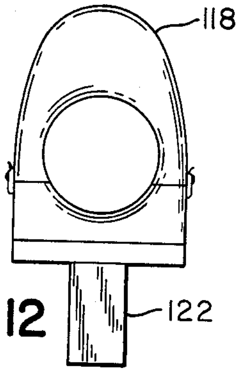
FIG. 12
FIG. 14
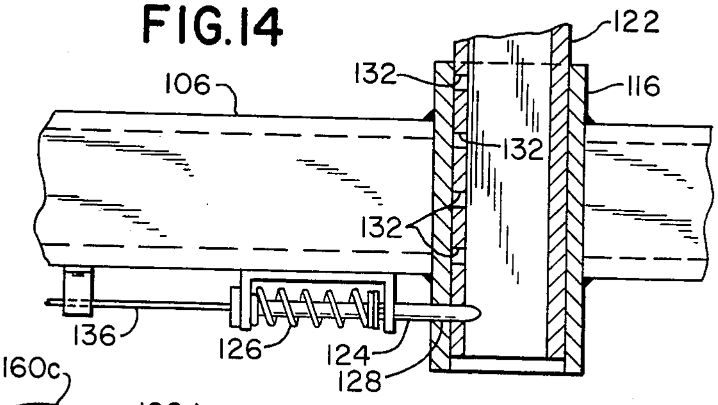
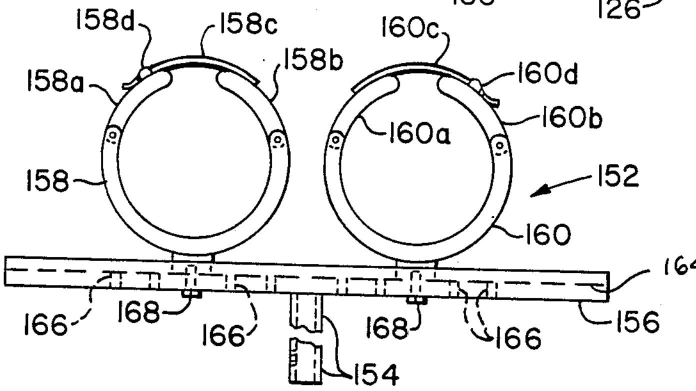
FIG. 15
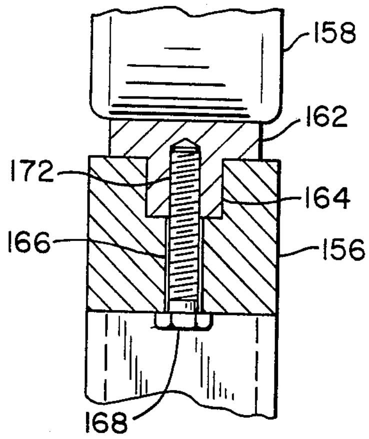
FIG. 16

THERAPEUTIC BED WITH TRACTION ASSEMBLY

BACKGROUND OF THE INVENTION

This invention relates to a therapeutic bed for home and institutional use and more particularly to a therapeutic bed which incorporates traction for patients with neck and back problems, such as fractures, and includes methods of alignment of certain orthopedic problems, promotion of postural drainage and other features for the convenience and treatment of patients.

Present devices for applying traction involve the use of pulleys and weights and skull pins for cervical traction; said devices hang outside the bed frame, are awkward and can be knocked loose or down, causing pain and interrupting the therapeutic steady pull traction requires.

A variety of beds have been designed with some of these problems in mind, such as those shown in U.S. Pat. Nos. 2,837,751, 3,430,956, 3,589,715, 3,722,010, and 4,188,677. None of these patents deals specifically with the application of traction but they show a variety of mechanisms for altering the position of the patient. They deal with specific types of adjustments, some of them are quite complicated.

SUMMARY OF THE PRESENT INVENTION

The present invention provides a bed with built-in capability controllable to apply, adjust, or release traction by use of devices attached to the bed frame and by altering the position of the bed itself using the angle of the bed and bed weight to provide a specific steady traction; or in less critical cases, to meet the patient's needs of convenience and comfort; to provide for postural drainage; all without the use of protruding pulleys and weights.

The therapeutic bed incorporating the principles of this invention is suitable for use in private homes as well as in such institutions as hospitals, nursing homes, and rest homes. The bed is suitable for use by persons with lung, neurological, and certain orthopedic problems; incorrect alignments, fractures, relief of pain where there is a compression of the discs, or vertebrae protrusion, and to achieve the advantages of inverse gravity.

Using the basic premise of the bed, body weight and angle for a more positive steady pull and positioning, included adjustable devices can hold a person by the feet for lower traction, alignment, or postural drainage, or by the jaw and skull bones via a special neck brace for cervical traction, thus avoiding the discomfort and possibility of infection common with skull pins.

In accordance with the principles of this invention, a preferred embodiment consists of a stationary frame, a movable frame with a mattress mounted on it, and a power unit for raising one end of the movable frame. On the movable frame on the raisable end may be mounted a neck brace on the exposed surface of the mattress, stirrups for holding the patient by the ankles, or special boots for holding the feet. A control is provided for the power unit so that the position of the movable frame can be adjusted for the amount of traction applied or where strict regulation is not required for comfort. The lower end of the movable frame has a hinged section which can be manually raised for comfort and to alleviate any problems made possible by a constant hanging position.

It is thus a principal object of this invention to provide a therapeutic bed having a variety of applications achieved by body weight, angle of the bed, and position of the user. Applications include the advantages of inverse gravity: rejuvenation through increased blood circulation, relief of symptoms of prolapsed organs, relief of pain common with back problems, etc, all without danger to the patient, as well as physical problems usually treated by other methods in an institutional setting.

Other objects and advantages of this invention will hereinafter become obvious from the following description of a preferred embodiment of this invention.

BRIEF DESCRIPTION OF THE DRAWINGS

FIG. 5 is an isometric view of a portion of the movable frame with the collar assembly mounted.

FIG. 6 is a front, elevation view of the collar assembly.

FIG. 6*a* is a side view of the collar shown in FIG. 6 with the neck and head of a patient.

FIG. 9 is an elevation view in partial section of foot stirrups mounted on the movable frame.

FIG. 11 is an isometric view partially schematic showing an alternative support arrangement for the neck brace.

FIG. 12 is a front elevation view of the neck brace supported as in FIG. 11.

FIG. 13 is a more detailed front elevation view of the neck brace support arrangement shown in FIG. 11.

FIG. 14 is a detail in section of the supporting cylinder shown in FIG. 13.

FIG. 15 is a front elevation view of an alternative foot support.

FIG. 16 is a detail in section of the construction to mount one of the foot supports shown in FIG. 15.

DESCRIPTION OF THE PREFERRED EMBODIMENT

Figure 1:
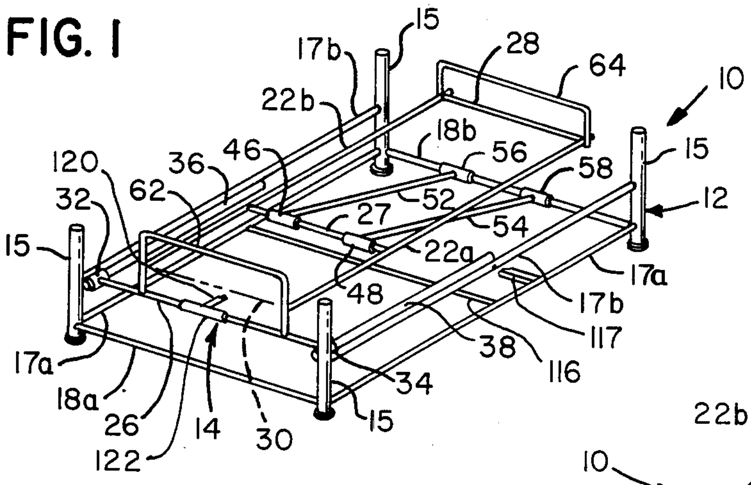
FIG. 1 is an isometric view of the frame construction of a preferred embodiment of the invention with the movable frame in a horizontal position partially schematic and with the drive assembly not shown.
Figure 2:
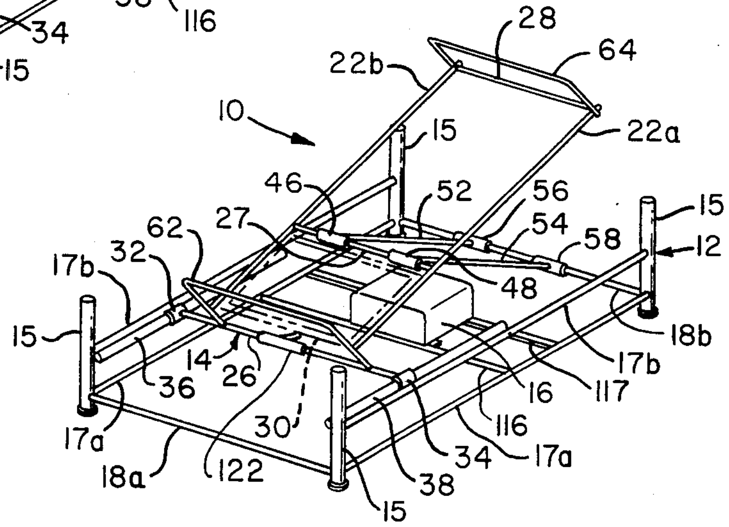
FIG. 2 is a similar isometric view of the bed in a raised position with a portion of the drive assembly shown.

Referring to FIGS. 1 and 2 there is illustrated therapeutic bed 10 consisting of a stationary frame 12, a movable frame 14, and a power unit 16 (seen in FIG. 2) mounted on stationary frame 12 in a manner to be explained later. In these figures, movable frame 14 is shown without a mattress or spring for convenience in revealing the details of construction comprising novel aspects of this invention.

Stationary frame 12 consists of four upright corner posts 15 interconnected by lengthwise lower and upper side rails 17*a* and 17*b* and transverse tubular members 18*a* and 18*b* to form a sturdy frame to support the remaining structure to be described.

Movable frame 14 is formed by a pair of lengthwise tubular members 22*a* and 22*b* and a plurality of transverse tubular members 26, 27, and 28.

Figure 3:
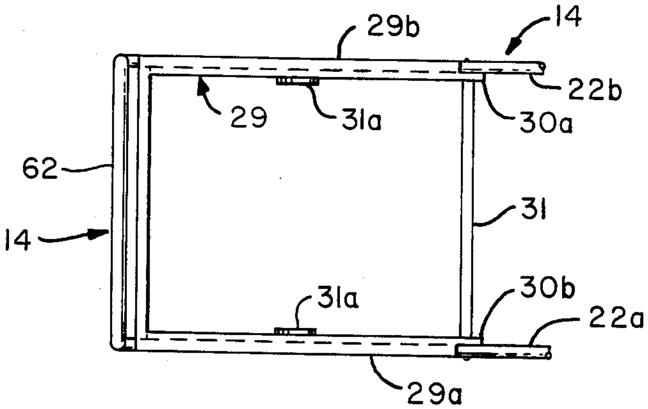
FIG. 3 is a plan view of the left end of the movable frame shown in FIGS. 1 and 2.
Figure 4:
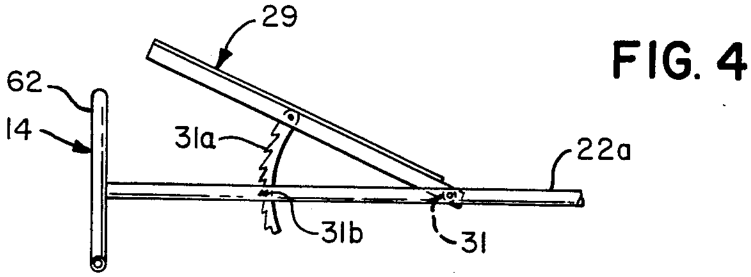
FIG. 4 is a side view of the portion of the frame shown in FIG. 3.

As best seen in FIGS. 3 and 4, the left end of movable frame 14 is provided with a pivoted section 29 with members 29*a* and 29*b* having flanges 30*a* and 30*b* resting on members 22*a* and 22*b* to support section 29 when retracted as seen in FIG. 3. Section 29 is pivoted about a cross member 31 while a toothed or serrated, arcuate shaped member 31*a* is provided to hold section 29 in any selected partially upright position as illustrated in FIG. 4, for which pins 31*b* extending from side rails 22 are provided as is understood in the art.

It is understood that frames 12 and 14 may be provided with additional structural elements to produce the proper degree of rigidity and support required. Frame 14 may be provided as necessary with side rails for the safety and comfort of the patient.

Movable frame 14 itself is pivoted in a manner about to be described. Transverse member 26 extends past lengthwise members 22*a* and 22*b* and terminates in a pair of cylindrical sleeves 32 and 34 riding on cylindrical slide bars 36 and 38 spaced from side rails 17*b*. The ends of transverse member 26 would be supported within pivots or bearings (not shown) in sleeves 32 and 34 to permit the pivoting being described. The ends of slide bars 36 and 38 would be provided with brackets (not shown) producing support from side rails 17*b*.

Mounted on transverse member 27 are a pair of rotatable sleeves 46 and 48 attached by arms 52 and 54 to rotatable sleeves 56 and 58 mounted on transverse member 18*b*. Thus, as movable frame 14 moves between the positions shown in FIGS. 1 and 2, powered in a manner to be described further below, pivoting takes place at sleeves 32 and 34, sleeves 46 and 48 on transverse member 27, and sleeves 56 and 58 on transverse member 18*b*.

Figure 7:
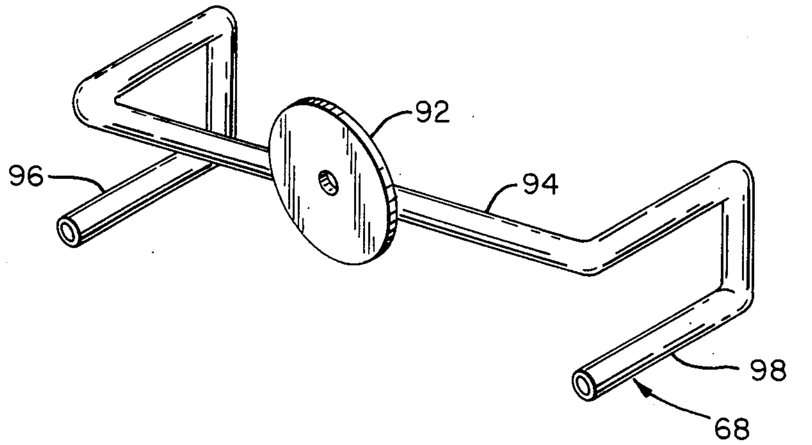
FIG. 7 is an isometric view of the foot support assembly.

Movable frame 14 is provided with a pair of inverted U-shaped foot and head rests 62 and 64, respectively. It will be noted from FIG. 5 that rest 64 is attached to the outside of lengthwise members 22*a* and 22*b* leaving the ends of members 22*a* and 22*b* accessible for engagement by either the neck supporting brace assembly 66 seen in FIG. 5, foot supporting assembly 68 seen in FIGS. 7 and 8, or ankle support assembly 69 shown in FIG. 9.

Neck supporting brace assembly 66 consists of a neck brace 72 mounted on a tubular cross member 74 with arms 76 and 78 configured to enter the open ends of tubular members 22*a* and 22*b* as seen in FIG. 5. Member 74 is sufficiently spaced from the plane of members 22*a* and 22*b* to accommodate the mattress and spring 75 shown in phantom in FIG. 5. The details of mattress and spring 75 are not shown as they are not part of this invention, being connected to frame 14 in any conventional fashion.

Neck brace 72 consists of a base 82 rigidly attached to member 74 and an upper member 84 whose position is secured by a pair of snap-on clasps 88 and 89 or any other type of arrangement desired. It is understood that brace 72 would be properly padded. The size of brace 72 would be selected to match the requirements of the patient. A different assembly 66 can be available for each size.

When traction is to be applied to the patient, he or she is placed face up on the bed with movable frame 14 in its horizontal position with the neck resting on base 82, as seen in FIG. 6*a*, and upper members 84 clamped down using clasps 88 and 89. Frame 14 is then rotated as shown in FIG. 2 until the weight of the patient provides the proper application of traction. A chart may be utilized to relate the angle of frame 14 to traction applied per unit weight of the patient.

Under some circumstances it may be desirable to support the patient with his or her feet raised. For this purpose, foot supporting accessory assembly 68 shown in FIGS. 7 and 8 for face up support, or ankle support assembly 69 in FIG. 9 for face down support may be employed.

Figure 8:
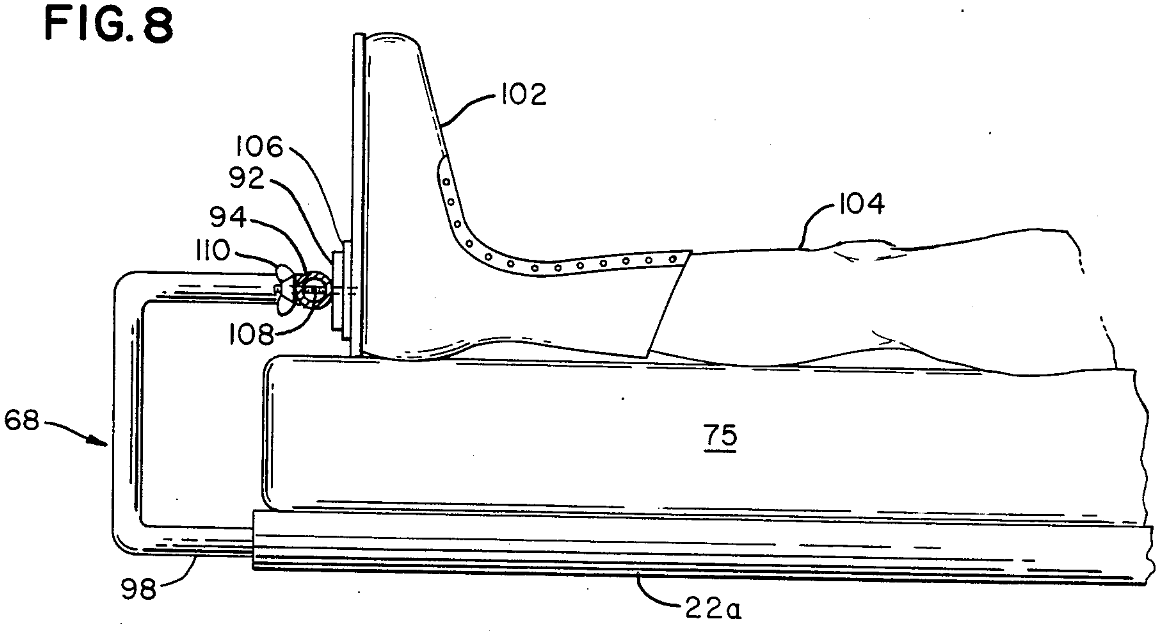
FIG. 8 is a side, elevation view in partial section of the foot support assembly mounted.

Assembly 68 is similar in construction to that of assebly 66 except that instead of brace 72 there is a plate 92 attached to cross member 94. Arms 96 and 98 would enter the end openings in members 22*a* and 22*b* as seen in FIG. 8. A special boot 102 is employed fitted to the foot 104 of the patient. The sole of boot 102 has a special plate 106 and a threaded screw 108 passing through plate 92 and cross member 94 threaded into plate 106 and attached to the sole of boot 102 with a finger nut 110 to tighten plates 92 and 106 against rotation. Thus boot 102 can be rotated to an angle which is most comfortable for the patient. The patient is resting back down on mattress 75 and frame 14 can be rotated so that the patient is resting head low supported by his feet.

When it is desirable to support the patient face down by the feet raising the latter above his or her head in order to effect postural drainage, as for example in the case of a patient afflicted with cystic fibrosis, the ankle support 69 shown in FIG. 9 would be employed. The patient would lie on the mattress face down and his or her ankles would be placed in the arc-shaped loops 111*a* and 111*b* formed in member 112 with vertically extending arms 112*a* and 112*b* supported on side members 22*a* and 22*b* at the right end of movable frame member 14 shown in FIGS. 1 and 2. Lower brackets 113*a* and 113*b* are pivoted on hinges 113*c* and 113*d*, respectively with respect to stationary brackets 114*a* and 114*b* mounted of arms 112*a* and 112*b*. The ankles are secured by a member 115 pivoted at a hinge 115*a* and locked by a suitable clasp 115*b*. Suitable clasps would also be provided for brackets 113*a*, 114*a*, and 113*b*, 114*b*, the design of such clasps not being a part of this invention.

In order to effect the movement of frame 14, mounted between a pair of cross members 116 and 117 between lengthwise members 17*a* is power unit 16. It is seen that when member 26 is drawn toward power unit 16, the other end of frame 14 will rise as shown in FIG. 2. When member 26 is pushed away from power unit 16, frame 14 will be lowered into its horizontal position as shown in FIG. 1.

Figure 10:
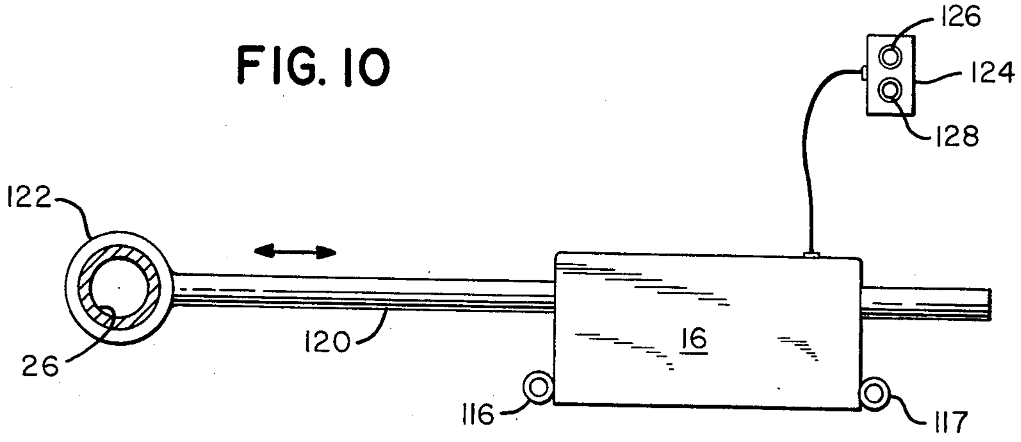
FIG. 10 is a side, elevation and partially schematic view of the motor drive assembly.

One way of effecting this movement is to utilize a drive as shown in FIG. 10. There it will be seen that power unit 16 mounted between members 116 and 117 has a powered arm 120 connected to a sleeve 122 on member 16 to effect movement of the latter shown by the arrows. It is understood that unit 16 may consist of electrical motor with a rack and pinion, arm 120 being part of the rack. Arm 120 may be at a slight upward angle to the left to insure smooth pivoting action. Control panel 124 with up and down buttons 126 and 128 would be placed on frame 14 or away from bed 10 at a location not in the reach of the patient.

Other provisions can also be made to power movable frame 14 if desired as the particular means of locomotion do not form a part of this invention. For example, a system of cables and pulleys can be arranged where desired. Further, provision if desired can be made to ease the load on the drive by providing a toggle arrangement at the beginning of movement to tilt up the movable frame at the start of movement.

In the operation of therapeutic bed 10, frame 14 would initially be in its horizontal position as shown in FIG. 1. Following the instruction of the physician, the technician would install the particular accessory prescribed, that is, either neck brace assembly 66, foot support assembly 68, or ankle support assembly 69. The patient would be placed on the bed. If the neck brace assembly 66 is in place, the nape of the patient's neck would be placed on base 82 and upper member 84 pivoted to enclose the neck below the chin and clamps 88 and 89 tightened to secure the neck. Then frame 14 would be rotated to the proper angle.

If the foot support assembly 68 is selected, where the patient is to remain face up, then the proper size boot 102 would be fitted on the patient and attached to plate 92 as shown in FIG. 8. Each boot 102 would be rotated to a position comfortable to the patient and each finger nut 110 tightened to hold each boot in the position selected. Frame 14 would then be raised to the position prescribed by the physician. Articulated section 29 illustrated in FIGS. 3 and 4 may be adjusted to an angle to improve the comfort of the patient.

If ankle support assembly 69 is employed, the patient as already noted is lying face down and movable frame 14 is adjusted to the angle selected by the physician.

Under certain circumstances it may be desirable to effect support of the head or ankles of the patient by a device supported under the mattress rather than the arrangements shown in FIGS. 5–9.

Alternative arrangements which can very conveniently be adjusted are shown in FIGS. 11–16.

Referring to FIG. 11, there is shown movable frame 14 with side rails 22a and 22b and a mattress and spring arrangement 202 illustrated in phantom. The mattress and spring arrangement 202 has an elongated opening 204 for a purpose about to be described.

Bridging side rails 22a and 22b is a bridging member 106 with sleeves 108 and 110 encompassing the side rails to permit its adjustment in the direction shown by double arrow A. Screw members 112 and 114 may be employed to lock member 106 in place once it is positioned.

Situated at the center of bridging member 106 is a hollow square cylinder or sleeve 116 for a purpose to be described below.

As seen in FIG. 12, neck brace 118 which is identical to neck brace 72 shown in FIGS. 6 and 6a is mounted on a pedestal 122 which is rectangular in cross section and designed to fit inside of sleeve 116. As best seen in FIGS. 13 and 14, the vertical position of neck brace 118 can be easily adjusted by sliding pedestal 122 up and down as required until brace 118 is located with respect to mattress 202 in a position most comfortable to the patient. A pull arrangement comprising a spring loaded pin 124 biased by a spring 126 through a hole 128 in sleeve 116 into one of a number of holes 132 in pedastal 122 holds brace 118 at the selected height. A pull 134 connected by cable 136 to pin 124 permits the latter to be withdrawn to readjust the position of pedestal 122.

In a similar manner, foot stirrup assembly 152 mounted on a pedestal 154 can be employed instead of neck brace 118 for mounting in cylinder 116 and adjusting both as indicated by arrows A in FIG. 11 and vertically as described above. Stirrup assembly 152 shown in FIG. 15 has certain other features which make it particularly convenient to use and adjust.

It will be seen that assembly 152 consists of a cross bar 156 mounted on pedestal 154 supporting a pair of ankle supports 158 and 160. Each support is provided with a pair of pivotal arms 158a, 158b and 160a, 160b, respectively, and a pair of flexible straps 158c and 160c which can be secured by conventional buckles 158d and 160d at the free end and attached to their respective pivotal arms at the other ends. This arrangement makes it possible to make adjustments for different ankle shapes and sizes.

In order to permit adjustment of the spacing between ankle supports 158 and 160, each of the latter is supported in such a way as to permit individual adjustment of spacing along cross bar 156. For example, as shown in FIG. 16, support 158 has a base 162 slidable in a slot 164 in the top of bar 156. At spaced intervals are holes 166 to accommodate a threaded screw 168 for engaging a threaded opening 172 in base 162. Thus to move either or both of supports 158 or 160, screw 168 is removed, the base is moved over to the holes desired, and screw 168 is then threaded back into base 162. Instead of a hex head, as illustrated, it is understood that a finger type wing head may be employed to avoid the need for a tool. The height of bar 156 would be adjusted so that it would move along the top surface of mattress and spring assembly 202.

It is understood that the stirrup design shown in FIG. 15 can also be employed in the arrangement shown in FIG. 9 with bar 156 extended out to be supported directly by side rails 22a and 22b.

It is thus seen that there has been provided a unique therapeutic bed capable of providing traction without the use of weights and without subjecting the patient to excessive discomfort, as well as including other features which make the bed useful in both a hospital and home environment. This bed can be employed in the home as well as in hospitals and other medical facilities. In addition, it is understood that the bed can be employed by persons who wish under certain circumstances to improve their comfort in bed.

While only certain preferred embodiments of this invention has been described, it is understood that many changes may be made without departing from the principles of this invention as defined in the claims which follow.

What is claimed is:

1. A therapeutic bed for use in the home and medical institutions comprising:

a. a stationary frame;

b. a movable frame mounted on said stationary frame for supporting a mattress;

c. powered means for raising one end of said movable frame;

d. means attached to the raising end of said movable frame for supporting a patient;

e. means for exercising control over said powered means for adjusting the position of said movable frame to adjust the angle of said patient;

f. means limiting the second end of said movable frame to movement in a horizontal plane, said limiting means including horizontally extending slide bars mounted on and adjacent one end of said stationary frame corresponding to the second end of said movable frame, and slides pivotally attached to the second end of said movable frame to slide on said slide bars;

g. pivots mounted on an intermediate part of said movable frame connected by arms to the other end of said stationary frame so that as the slides on said movable frame move on said slide bars said pivots will cause the first end of said movable frame to rise or lower; and h. means connecting said powered means to the second end of said movable frame upon being activated to move the sliding end of said movable frame.

2. The therapeutic bed of claim 1 in which said supporting means includes brace means for supporting the patient under the chin, the angle at which said movable frame is adjusted thereby selecting the traction applied to said patient.

3. The therapeutic bed of claim 2 in which said brace means includes a base upon which the nape of the neck rests and an upper member to enclose the neck under the chin.

4. The therapeutic bed of claim 3 having a mattress with an opening therethrough in which said neck brace means is supported by a pedestal passing through the opening in said mattress, and means to permit both vertical adjustment of said brace means and movement along the length of said bed.

5. The therapeutic bed of claim 1 in which said supporting means includes means to support the patient by the feet.

6. The therapeutic bed of claim 5 in which the feet supporting means includes boots worn by the patient and means to adjust the angular position of the boots for the comfort of the patient.

7. The therapeutic bed of claim 1 including means to support the patient by the ankles.

8. The therapeutic bed of claim 7 having a mattress with an opening therethrough in which said ankle supporting means includes a pair of ankle braces mounted on a cross bar, means to permit the ankle braces to be moved along said cross bar, means to support said cross bar passing through the opening in said mattress, and means to permit both vertical adjustment of said cross bar and movement along the length of said bed.

* * * * *